US 6,528,316 B1

(12) United States Patent
Gosling

(10) Patent No.: US 6,528,316 B1
(45) Date of Patent: Mar. 4, 2003

(54) CONTROL OF SOLID CATALYST ALKYLATION PROCESS USING RAMAN SPECTROSCOPY

(75) Inventor: Christopher D. Gosling, Roselle, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/631,192

(22) Filed: Aug. 2, 2000

(51) Int. Cl.⁷ .............................................. G01N 35/08
(52) U.S. Cl. ..................... 436/55; 436/164; 436/171; 250/339.03; 356/301
(58) Field of Search ............ 250/338.1, 339.01–339.12; 356/51, 301, 303; 436/55, 164, 171

(56) References Cited

U.S. PATENT DOCUMENTS

| | | | |
|---|---|---|---|
| 2,527,122 A | 10/1950 | Heigl et al. ..................... 88/14 |
| 5,073,653 A | 12/1991 | Butler ......................... 585/449 |
| 5,081,323 A | 1/1992 | Innes et al. .................. 585/449 |
| 5,292,981 A | 3/1994 | Huang et al. ................ 585/722 |
| 5,452,232 A | * 9/1995 | Espinosa et al. ............. 364/498 |
| 5,684,580 A | 11/1997 | Cooper et al. ............... 356/301 |
| 5,712,481 A | 1/1998 | Welch et al. ........... 250/339.12 |
| 6,096,533 A | * 8/2000 | Heald et al. ................... 436/40 |

* cited by examiner

*Primary Examiner*—Jill Warden
*Assistant Examiner*—Yelena Gakh
(74) *Attorney, Agent, or Firm*—John G. Tolomei; Frank S. Molinaro; Maryann Maas

(57) ABSTRACT

An advanced method for controlling a solid catalyst alkylation process has been developed. At multiple locations throughout the alkylation process including multiple locations within the reaction zone, on-line Raman spectroscopy is used to measure the concentration of alkene. Operating parameters are adjusted depending upon the concentration of alkene measured, or the conversion of alkene determined. Different operating parameters are adjusted depending upon the alkene concentration or conversion measured at different locations thus pairing a particular operating parameter with an ideal location for alkene measurement and control.

14 Claims, 1 Drawing Sheet

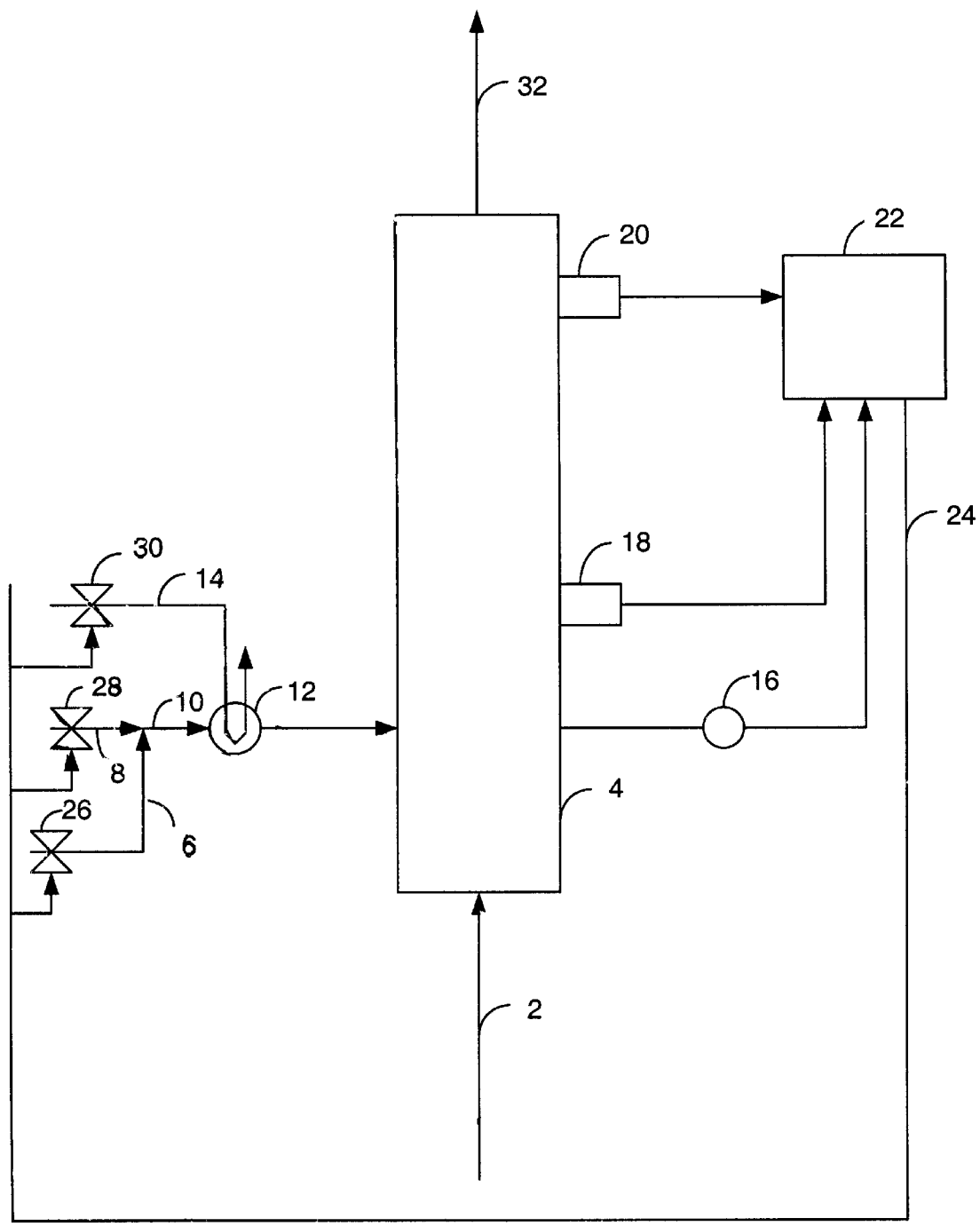

US 6,528,316 B1

CONTROL OF SOLID CATALYST ALKYLATION PROCESS USING RAMAN SPECTROSCOPY

FIELD OF THE INVENTION

The invention is an advanced method for controlling a solid catalyst alkylation process using Raman spectroscopy.

BACKGROUND OF THE INVENTION

Alkylate is the alkane product mixture of the alkylation reaction of an alkene and an alkane. The alkene typically has from 2 to 6 carbon atoms, but may have as many as 20 carbon atoms. The alkane typically has from 4 to 6 carbon atoms. One important use of an alkylate is as a component in motor fuel, and its importance continues to grow with strict government regulations on historical octane number boosters such as lead anti-knock additives and aromatics. In order to boost the octane number of the motor fuel octane, it is desirable for the alkylate to have a high octane number, and, therefore, branched and multi-branched alkenes such as trimethylpentanes are the preferred components of the alkylate. Alkylation processes require a strong acid catalyst such as sulfuric acid or liquid hydrogen fluoride. More recently, due to environmental pressure, solid alkylation catalysts have been developed (see U.S. Pat. No. 2,999,074). Other alkylation reactions may involve the reaction of the alkene with an aromatic hydrocarbon, the most common of which is benzene.

Common solid catalysts used in alkylation processes have the drawback of rapid deactivation and require frequent regeneration. Once the catalyst begins to deactivate, its activity falls off almost exponentially. If the catalyst is not removed or regenerated, the conversion of the alkylation process significantly and quickly decreases, and the reactants contaminate the alkylate. Such contamination is to be avoided since feed material is wasted and, furthermore, it may be difficult to remove the reactants from other reactor effluent components. Also, it is beneficial to curtail catalyst deactivation early to prevent severe degradation of the catalyst.

In general, measuring the composition of the effluent of a reactor during the course of a chemical reaction is a common way to monitor the reaction occurring in a reactor. Many processes are conducted over a period of time and the resulting compounds in a reactor effluent may vary over the course of the chemical reaction. For example, when a reaction is initiated in a reactor, the concentration of a particular material may be at an initial level. As the process stabilizes the concentration of the material may undergo dramatic changes and then reach a point where changes in the concentration of the material are slow or gradual. Subsequent rapid changes in the concentration of the material may indicate a problem with the reaction such as rapid deactivation of the catalyst or a process upset. Control of process parameters may be based on changes in the composition of a reactor effluent during the course of the chemical reaction. For example, gradual decreases in the concentration of the desired product in a reactor effluent may indicate catalyst aging and may trigger periodic adjustments to the operating temperature of the reactor in order to increase, or reduce the rate of decrease, of the desired component in the effluent. Therefore, during the course of a chemical reaction, the concentration changes occurring as a result of the chemical reaction are often monitored by measuring the effluent of the reactor, see for example, U.S. Pat. Nos. 5,712,481 and 5,684,580.

In alkylation processes, monitoring the concentration of the alkene in the alkylate exiting the reactor is a common way to detect the deactivation of the catalyst. Gas chromatography has been used to measure the concentration of alkene in the alkylate. As the catalyst deactivates, the concentration of alkene in the alkylate increases and, at a particular stage of deactivation, the catalyst needs to be regenerated to prevent excessive alkenes in the product alkylate. In a commercial test, the lifetime of a catalyst can be as short as one minute, but is generally between about one minute and about five minutes. Even when operating on-line, the gas chromatographic analysis typically requires at least thirty minutes and during those thirty minutes the alkylate may contain large amounts of unconverted alkenes and the catalyst may become seriously deactivated.

As compared to control methods based on monitoring reactor effluent, the present invention provides advanced control through measuring the alkene concentrations by Raman spectroscopy at multiple locations within the alkylation process including at least two locations within the reaction zone(s) as well as at the alkylate product stream. The virtually instantaneous results allow for the adjustment of operating parameters or regeneration of catalyst before the alkylate is unacceptably contaminated with reactants, Furthermore, different operating parameters are adjusted depending upon the alkene concentration measured at different locations thus pairing a particular operating parameter with an ideal location for alkene measurement and control. Lastly, Raman spectroscopy is uniquely suited for use in alkylation processes since the other non-alkene components typically found in alkylation processes have weak Raman effects and little fluorescence.

SUMMARY OF THE INVENTION

The purpose of the invention is to provide an advanced method for controlling a solid catalyst alkylation process. At multiple locations throughout the process, including multiple locations within the reaction zone, on-line Raman spectroscopy is used to measure the concentration of alkenes. For example, an embodiment of the invention is one requiring measuring the Raman spectrum on-line over wave numbers from about 150 $cm^{-1}$ to about 1850 $cm^{-1}$ of: the reaction mixture in the reaction zone at a location near a feed input location, the reaction mixture in the reaction zone at a location downstream of the feed input location, and the alkylate. The concentration of alkene is then determined in: the reaction mixture at the location near the feed input location, A, the reaction mixture at the location downstream of the feed input location, B, and the alkylate, C, using the Raman spectra and a first, second, and third algorithm. The concentration, A, is compared with a predetermined range of desired concentrations of alkene in the reaction mixture at the location near the feed input location, D, and adjustment made, within established alkane feed stream flow rate control limits, when A is not within C, to the flow rate of the alkane feed stream according to a fourth algorithm to cause A to fall within D. The conversion of alkene occurring between the location near the feed input location and the location downstream of the feed input location, E, is determined by difference between A and B, and E is compared with a predetermined range of desired alkene conversion values, F, and adjustment made, within established alkene feed stream flow rate control limits and reactor temperature control limits, when E is not within F, to an operating parameter selected from the group consisting of flow rate of the alkene feed stream, reactor temperature, and a combination thereof, according to a fifth algorithm to cause E to fall within F. C is compared with a predetermined range of desired concentrations of alkene in the alkylate, G, and adjustment made, when C is not within G, to an operating parameter selected from the group consisting of severity of catalyst regeneration conditions, treatment of the feed streams, frequency of catalyst regeneration, rate of catalyst regeneration, and a combination thereof, according to a sixth algorithm to cause C to fall within G and to reset operating parameters selected from the group consisting of the flow rate of the alkane feed stream, the flow rate of the alkene feed stream, the reactor temperature, and a combination thereof, to within their respective established control limits.

Another embodiment of the invention is one where the alkylation process contains at least two serially-connected sub-reaction zones $z_i$ where i is an integer from 2 to n, each having an independent alkene feed stream and an alkane feed stream. In this embodiment, the Raman spectrum is measured on-line over wave numbers from about 150 cm$^{-1}$ to about 1850 cm$^{-1}$, of: the reaction mixture in each sub-reaction-zone $z_i$ at a location near the feed input location of that sub-reaction-zone $z_i$ the reaction mixture in each sub-reaction-zone $z_i$ at a location downstream of the feed input location of that sub-reaction-zone $z_i$ and the alkylate. The concentration of alkene in: the reaction mixture in each sub-reaction-zone $z_i$ at the location near the feed input location of each sub-reaction-zone $z_i$, $A_{z_i}$, the reaction mixture in each sub-reaction-zone $z_i$ at the location downstream of the feed input location of each sub-reaction-zone $z_i$, $B_{z_i}$, and at the alkylate, C, is determined using the Raman spectra and a first, second, and third algorithm. $A_{z_i}$ is compared with a predetermined range of desired concentrations of alkene in the reaction mixture of the sub-reaction-zone $z_i$ at the location near the feed input location of the sub-reaction-zone $z_i$, $D_{z_p}$, and adjustment made, within established alkane feed stream flow rate control limits for sub-reaction-zone $z_i$ when $A_{z_i}$ is not within $D_{z_i}$ to the flow rate of the alkane feed stream to sub-reaction-zone $z_i$ according to a fourth algorithm to cause $A_{z_i}$ to fall within $D_{z_i}$. The conversion of alkene occurring between the location near the feed input location and the location downstream of the feed input location of each sub-reaction-zone $z_i$, $E_{z_i}$, is determined from the difference between $A_{z_i}$ and $B_{z_i}$, and $E_{z_i}$ is compared with a predetermined range of desired alkene conversion values for each sub-reaction-zone $z_i$, $F_{z_p}$, and adjustment made, within established alkene flow rate control limits for sub-reaction-zone $z_i$ and temperature control limits for sub-reaction-zone $z_i$, when $E_{z_i}$ is not within $F_{z_p}$, to an operating parameter selected from the group consisting of flow rate of the alkene feed stream to sub-reaction-zone $z_i$, temperature of sub-reaction-zone $z_i$, and a combination thereof, according to a fifth algorithm to cause $E_{z_i}$ to fall within $F_{z_i}$. C is compared with a predetermined range of desired concentrations of alkene in the alkylate, G, and adjustment made, when C is not within G, to an operating parameter selected from the group consisting of severity of catalyst regeneration conditions, treatment of the feed streams, frequency of catalyst regeneration, rate of catalyst regeneration, and a combination thereof, according to a sixth algorithm to cause C to fall within G and to reset operating parameters selected from the group consisting of the flow rate of the alkane feed streams to the sub-reaction zones, the flow rate of the alkene feed streams to the sub-reaction-zones, the temperatures of the sub-reaction zones, and a combination thereof, to within their respective established control limits.

BRIEF DESCRIPTION OF THE DRAWING

The drawing is a generic representation of a single sub-reaction zone of an alkylation process modified and operated in accordance with the present invention. The drawing has been simplified by the deletion of a large number of pieces of apparatus customarily employed on processes of this nature which are not specifically required to illustrate the performance of the present invention.

DETAILED DESCRIPTION OF THE INVENTION

In general terms, the invention is a method for controlling an alkylation process using Raman spectroscopy to measure the concentration of alkene at multiple points throughout the alkylation process including multiple points within the reaction zone and then adjusting operating parameters to maintain the concentration of alkene at each location, or the amount of conversion of alkene between two locations, within a desired range of alkene concentrations or conversions for that location(s). At a minimum, the alkene concentration measurements are preformed at (1) a point within the reaction zone near the input of the feed streams, (2) a point within the reaction zone but downstream of the input of the feed streams, and (3) the alkylate product stream. The operating parameters adjusted are different depending upon the location of the alkene measurement. Where the alkylation process contains more than one serially-connected sub-reaction zone and each sub-reaction zone receives independent feed introduction, the alkene concentration is measured via Raman spectroscopy within each sub-reaction zone at a position near the feed introduction and again downstream of the feed introduction, in addition to at the overall reaction zone alkylate product stream. The alkylation process begins with introducing at least the two reactants to a reactor containing a solid catalyst effective to catalyze the alkylation reaction. The following description will focus on an alkylation process where an alkene is reacted with an alkane, but the invention may also be applied to an alkylation process where an alkene is reacted with an aromatic hydrocarbon such as benzene. Typically each reactant, the alkene and the alkane, is introduced in a separate feed stream so that the flow rate of each stream can be independently controlled. Solid alkylation catalysts are known in the industry and include: the reaction product between one or more of the metal halides active as Friedel-Crafts catalyst and a refractory inorganic oxide having surface hydroxyl groups where the refractory inorganic oxide also contains dispersed thereon a metal having hydrogenation activity for olefins (see U.S. Pat. No. 2,999,074, incorporated by reference), $BF_3$ on alumina, sulfated zirconia, tungstated zirconia, and zeolites. The alkylation process may be operated in a variety of modes such as batch, swing bed, cyclic, and continuous. The preferred mode of operation is the continuous transport mode. It is preferred that the multiple serially-connected reaction zones are used with each zone having independent reactant feed streams. The operating conditions are typically those necessary to maintain the process in a liquid phase.

As the alkene and alkane reactants contact the catalyst, the alkylation reaction takes place and alkylation products are formed; such products are referred to as "alkylate". Some of the alkene reactants, however, may react with other alkene reactants and form undesirable by-products, and particular by-products deposit on the surface of the catalyst causing deactivation and increased amounts of unreacted alkene in the reaction mixture and in the alkylate product stream. Once deactivation has begun, it tends to continue very rapidly and usually within 10 to 20 minutes the activity of the catalyst becomes unacceptable. If the catalyst is allowed to significantly deactivate, severe regeneration conditions are necessary to restore acceptable activity. Temperatures up to 100° C. above the normal regeneration temperatures may be required, and the time for regeneration may be extended to several hours. Complete deactivation of the catalyst may also shorten the useful lifetime of the catalyst due to the severe regeneration conditions and the potential decrease in recoverable activity with each regeneration. Deactivation of the catalyst may also be caused by a contaminant in a feed stream that acts as a catalyst poison. As the poison deactivates the catalyst, the activity of the catalyst decreases and the amount of unreacted alkene in the reaction mixture increases. With further deactivation of the catalyst, unreacted alkene is found in the product alkylate. Therefore, monitoring the alkene concentration in the reaction mixture and in the product alkylate helps to detect the presence of a catalyst poison.

Currently, catalyst deactivation is detected by gas chromatographic measurements of the concentration of alkene at only one location: at the alkylate product. The gas chromatograph is usually operated on-line where a sample of alkylate is routed directly from the effluent line to the gas chromatograph. On-line operation eliminates the delay involved in sending an effluent sample to a laboratory for analysis. However, even with on-line operation, the chromatographic analysis time requires approximately 30 to 60 minutes. Therefore, when using gas chromatography, the alkene concentration results are always at least 30 minutes old. That is, the results indicate the alkene concentration in the reactor effluent as it was 30 minutes in the past. This can be a problem since, during the 30 or more minute time delay, the catalyst may have greatly deactivated. A faster method of alkene measurement and an increased number of strategic measurement locations paired with the adjustment of selected optimum operating parameters provide for greatly enhanced control over the alkylation process.

Raman spectroscopy is a well-known, rapid, and quantitative method of analysis that involves measuring the Raman effect or Raman scattering. Scattering occurs as a result of a beam of light impinging on a sample. The beam of light is virtually monochromatic or predominately of a single wavelength. The scattering is of several different types, with the major type being Rayleigh scattering where the wavelength of the scattered light is the same as the incident light. Raman scattering occurs when the wavelength of the scattered light is different from that of the incident light due to photons being absorbed by the sample and then re-emitted at higher or lower wavelengths. To be Raman active, there must be a change in polarizability during molecular vibration. A Raman spectrum of a substance shows the Rayleigh and Raman scattered light spread across a wavelength range. The Raman lines appear on both sides of a single Rayleigh line. The Raman lines on the low frequency side of the Rayleigh line are more intense than those on the high frequency side and are called Stokes lines, while the Raman lines on the high frequency side of the Rayleigh line are less intense and are called anti-Stokes lines. Species identification may be made by comparing the Raman wave number shift in the sample to those of a known standard. Qualitative analysis may be performed by comparing the intensities of Raman lines in a sample with those of a known standard. Since the relationship of intensity to concentration is generally linear, quantitative analysis can be performed as well. For a more detailed discussion of Raman spectroscopy see, Willard, H. H.; Merritt, L. L. Jr.; Dean, J. A.; Settle, F. A. Jr. *Instrumental Methods of Analysis;* Wadsworth: Belmont, Calif., 1981; Chapter B.

Raman spectroscopy is known to be an accurate technique for measuring alkenes in hydrocarbon mixtures (see U.S. Pat. No. 2,527,122). However, many common refinery processes contain fluorescent compounds that would completely mask the Raman spectrum and thereby prevent Raman spectroscopy from being used in a great number of applications, (see McCreery, R. L. *American Laboratory,* February 1996, 34X–34JJ). In stark contrast to this general belief, Raman spectroscopy is uniquely suited to measuring the amount of alkene in the alkylate due to the typical composition of alkylate. Other than alkenes, alkylate generally contains few components that have strong Raman effects in the spectral region used for alkene determination, specifically from about 150 $cm^{-1}$ to about 1850 $cm^{-1}$. For example, alkylate usually has only a trace concentration of aromatic compounds which have strong Raman signals at the wave numbers of interest here. Also, alkylate does not usually contain components that exhibit fluorescence which overwhelms Raman signals. Therefore, the unique composition of alkylate makes Raman spectroscopy the technique of choice. Furthermore, results from Raman spectroscopy are rapidly available since analysis times range from 20 milliseconds to 1 minute with the average analysis time being about 30 seconds. A 30-second analysis time is preferred as compared to a 20 millisecond analysis since the signal to noise ratio is greater with longer analysis times. As discussed above, rapid analysis is important for early detection of catalyst deactivation, and being able to determine the alkene concentration in the alkylate every 30 seconds allows the process operating parameters to be controlled and adjusted so as to prevent significant deactivation of the catalyst and contamination of the alkylate. In the instant invention, the Raman spectrometer is operated on-line to measure the Raman spectrum of at least (1) the reaction mixture in the reaction zone at a location near the input location of the feed streams, (2) the reaction mixture in the reaction zone at a location downstream of the input location of the feed streams, and (3) the alkylation reactor effluent or alkylate. In alkylation processes having multiple sub-reaction zones where each sub-reaction zone received independent introduction of the feed streams, it is preferred that the Raman spectrum be measured in (1) the reaction mixture in each subreaction zone at a location near the input location of the feed streams, (2) the reaction mixture in each sub-reaction zone at a location downstream of the input location of the feed streams and (3) the overall alkylation reactor effluent or alkylate. Note that the Raman spectrum is measured at multiple locations within each sub-reaction zone and then at a single final location in the alkylate stream withdrawn as the product of the entire multiple sub-reaction zone alkylation reactor. "On-line" as used herein, is meant to include the situation where the analysis incorporates a probe placed immediately adjacent to, or immersed in, a process stream. At the locations where particles are typically contained in the process stream, such as in reaction zones, the Raman spectroscopy probe may be placed in a filtered slipstream. A single Raman spectrometer with multiple probes positioned at different locations within the alkylation process may be used, or a complete Raman spectrometer with probe may be positioned at each measurement location within the alkylation process. For ease of understanding, the following description will assume a single Raman spectrometer with multiple probes at multiple locations within the alkylation process.

Generally, the Raman spectrometer will have the following components: a light source, multiple probes each containing a probe head, a dispersive or diffractive element, a signal multiplier, a detector, and a processor. Because of difficulties in spectral separation, the light source must provide essentially monochromatic light and the wavelength must be stable. Today, many different types of lasers are available to provide monochromatic light including both ion tube lasers and solid state lasers. Examples of ion tube lasers are air cooled $Ar^+$, krypton, and He—Ne; and examples of solid state lasers include doubled Nd:YAG, external cavity diode, and internal cavity diode. The preferred ion tube lasers are the $A^+$ and He—Ne. The preferred solid state laser is the external cavity diode laser operating at approximately 780 nanometers. Note that lasers do not provide totally monochromatic light. For example, the He—Ne laser produces radiation "centered" around 6328 angstroms. The Rayleigh light does not form a single line at 6328 angstroms, but forms a band centered on that value with the appearance of a Gaussian curve.

The light generated by the laser is conducted to a probe. A variety of Raman probes are available for use in the invention. One type of probe, the backscatter Raman probe, could be affixed to a quartz or sapphire window in the housing carrying the effluent stream. The window should be the minimum thickness allowable according to process conditions, usually one-half inch or less. The diameter of the window should be only slightly larger than the outer diameter of the probe, usually one-half inch or less. The junction of the probe and the window should be enclosed or shielded so that no extraneous light is exposed to and conducted by the probe. In the backscatter Raman probe, an exciting optical fiber is surrounded by return optical fibers. The exciting light is conducted through the exciting optical fiber and is scattered in all directions when it impinges on the effluent sample. The scattered light that enters the return optical fibers is it conducted to the Raman spectrometer. A detailed discussion of Raman backscatter probes may be found in U.S. Pat. No. 4,573,761. Recently, probes that can be immersed directly in effluent streams have become available (see Pelletier, M; Davis, K. *American Laboratory* February 1996, 34C–34N). The advantage of immersing the probe directly in a stream is that the window in the housing of the stream may be eliminated.

Alternately, two windows may be placed in the effluent housing at a right angle to each other (90° apart on a pipe). The exciting light is passed through the first window, and the scattered light is collected through the second window. For this type of configuration, a custom probe could be used (see Long, D. A. *Raman Spectroscopy;* McGraw-Hill: New York, 1977). Furthermore, with this "perpendicular-type" configuration, one is able to measure the depolarization ratios which are helpful in identifying specific alkenes. Further information involving determining depolarization ratios can be found in Spencer, K. M.; Edmonds, R. B.; Rauh, R. D., Carrabba, M. M. *Analytical Chemistry* 1994, 66(8), 1269–1273.

Typically, on-line Raman probes contain probe heads which contain filters to remove extraneous wavelengths that might be present in the excitation light from the laser and to remove any Raman signal induced in the excitation fiber or in the window. Similarly, the probe head may filter out the Rayleigh scatter. Additional details on probe head options may be found in Marteau, P.; Zanier, N. *Spectroscopy* 1995, 10(7), 26–31 and Pelletier, M; Davis, K. *American Laboratory* February 1996, 34C–34N. Another probe option would be to incorporate a lens assembly to focus the exciting light at different depths within the effluent. See also, McCreery, R. *American Laboratory* February 1996, 34X–34JJ.

The Raman scatter collected by the probes is sequentially conducted from each probe to the entrance slit of the monochromator of a Raman spectrometer. The monochromator is traditionally defined as an apparatus having a dispersive or diffractive element, a single entrance slit and a single exit slit. The Raman scatter, having passed though the entrance slit, contacts the means to produce monochromatic optical radiation from the polychromatic optical radiation. Suitable means include common dispersive or diffractive elements. Prisms are one example of such dispersive or diffractive elements. Prisms have been made of such materials as quartz, crystalline sodium chloride, potassium bromide, cesium bromide, and lithium fluoride. Diffraction gratings are another example of suitable dispersive or diffractive elements, and the grating may be a transmission grating or a reflection grating.

The detector used in the spectrometer is positioned in optical alignment with the dispersed or diffracted polychromatic light passing through the exit slit of the monochomoter and may be any commonly known detector capable of responding to the optical radiation wavelength range of interest, specifically wavelengths greater than the excitation laser wavelength. A suitable Raman wave number shift range is from about 150 $cm^{-1}$ to about 1850 $cm^{-1}$. For example, suitable detectors include charge-coupled devices (CCD), trialkali photocathodes, extended red-sensitive multialkali cathodes, gallium arsenide photocathodes, and photomultiplier tubes. Generally, the preferred detector is the CCD.

Each Raman spectrum sensed by the detector is compared to known standards and via calibration the concentration of alkene at each probe location is determined. Calibration techniques are well known in the art. Examples of suitable calibration algorithms include partial least squares regression models, principal components regression, multiple linear regression, ratioed peak areas, multivariate statistical methods, principal component analysis, and neural networks. See U.S. Pat. No. 2,527,122, Marteau, P.; Zanier, N. *Spectroscopy* 1995, 10(7), 26–31; Cooper, J. B.; Wise, K. L.; Grove, J.; Welch, W. T. *Analytical Chemistry* 1995, 67(22), 4096–4100; Cooper, J. B.; Flecher, P. E.; Vess, T. M.; Welch W. T. *Applied Spectroscopy* 1995, 49(5), 586–592; de Bakker, C. J.; Fredericks P. M. *Applied Spectroscopy* 1995, 49(12), 1766–1771.

The alkene concentration determinations are used to adjust operating parameters and thereby control the alkylation process. Different operating parameters are adjusted based upon the alkene determinations made at each location within the alkylation process. The first alkene concentration measurement is conducted via Raman spectroscopy on the reaction mixture within a reaction zone at a location near the feed input to that reaction zone. If the measured alkene concentration falls within a predetermined desired range, no operating parameter adjustment is necessary. However, if the measured alkene concentration does not fall within the predetermined desired range, the flow rate of the alkane feed stream is adjusted according to an algorithm so that the measured alkene concentration at the location near the feed input now falls within the predetermined desired range. Suitable algorithms that may be used in determining the adjustment include neural networks, expert systems, multivariate regression, and partial least squares. The flow rate of the alkane feed stream may be adjusted only within established control limits.

Where multiple sub-reaction zones, $z_i$, where i is an integer from 2 to n, are used, an alkene concentration measurement, $A_{z_i}$, is conducted via Raman spectroscopy on the reaction mixture within each sub-reaction zone at a location near the feed input to that sub-reaction zone. If the measured alkene concentration falls within a predetermined desired range for that sub-reaction zone, no operating parameter adjustment is necessary. However, if the measured alkene concentration does not fall within the predetermined desired range for that sub-reaction zone, the flow rate of the alkane feed stream to that sub-reaction zone is adjusted according to an algorithm so that the measured alkene concentration at the location near the feed input for that sub-reaction zone now falls within the predetermined desired range for that sub-reaction zone. Suitable algorithms are the same as those for the single reaction zone embodiment. The flow rate of the alkane feed stream may be adjusted only within established control limits for that sub-reaction zone. When the alkylation reaction involves the reaction of an alkene and an aromatic hydrocarbon, the flow rate of the aromatic hydrocarbon independent feed stream is adjusted when necessary in response to the alkene concentration measured at a location near the feed input to the reaction zone(s) as described above for the alkene feed stream.

The next alkene concentration measurement is conducted via Raman spectroscopy at a location downstream from the location of the feed input to the zone. The downstream location is chosen so that at least about 70 percent of the expected alkylation reaction in that zone has occurred. Typically, when operating in the continuous mode, the location will be downstream at a distance equal to approximately two to three times the diameter of the riser. The amount of alkene conversion occurring in the reaction zone between the location of the first measurement and the downstream location is then calculated by difference using the two alkene measurements. The calculated alkene conversion is compared to a predetermined desired range of alkene conversions. If the alkene conversion falls within the predetermined desired range, no operating parameter adjustment is necessary. However, if the alkene conversion does not fall within the predetermined desired range, the flow rate of the alkene feed stream, the reactor temperature, or a combination thereof is adjusted so that the alkene conversion now falls in the desired range. Again, suitable algorithms that may be used in determining the adjustment include neural networks, expert systems, multivariate regression, and partial least squares. The flow rate of the alkene feed stream and the reaction zone temperature may be adjusted only within established control limits.

In the case where multiple sub-reaction zones, $z_i$, where i is an integer from 2 to n, are employed, the alkene concentration measurements, $B_{z_i}$, are conducted via Raman spectroscopy at a location downstream from the location of the feed input to each sub-reaction zone. The amount of alkene conversion occurring in each sub-reaction zone between the location of the first measurement and the downstream location is then calculated by difference using the two alkene measurements. The calculated alkene conversion of each sub-reaction zone is compared to a predetermined desired range of alkene conversions for each sub-reaction zone. If the alkene conversion in a sub-reaction zone falls within the predetermined desired range for that sub-reaction zone, no operating parameter adjustment is necessary. However, if the alkene conversion in a sub-reaction zone does not fall within the predetermined desired range for that sub-reaction zone, the flow rate of the alkene feed stream to that sub-reaction zone, the temperature of that sub-reaction zone, or a combination thereof is adjusted so that the alkene conversion in the sub-reaction zone now falls in the desired range for that sub-reaction zone. Again, suitable algorithms that may be used in determining the adjustment include neural networks, expert systems, multivariate regression, and partial least squares. The flow rate of the alkene feed streams and the sub zone temperatures may be adjusted only within established control limits for each sub-reaction zone.

The third alkene concentration measurement is conducted via Raman spectroscopy on the alkylate effluent stream exiting from the reaction zone. This single measurement of the overall alkylate effluent stream is performed in the embodiment having one reaction zone as well as the embodiment having multiple sub-reaction zones. As before, if the measured alkene concentration falls within a predetermined desired range, no operating parameter adjustment is necessary. If the measured alkene concentration does not fall within the predetermined desired range, an operating parameter selected from the group of severity of catalyst regeneration conditions, treatment of the feed streams, frequency of catalyst regeneration, rate of catalyst regeneration, or a combination thereof is adjusted so that the alkene concentration now falls within the desired range. Suitable algorithms that may be used in determining the adjustment include neural networks, expert systems, multivariate regression, and partial least squares.

It is expected that the alkene concentration in the alkylate will fall outside the desired range for the alkylate when the control limits on the adjustments to the flow rates of the feeds and the reaction zone temperature have been reached. In that case, adjustments to the severity of catalyst regeneration conditions, the treatment of feed streams, the frequency of catalyst regeneration, the rate of catalyst regeneration, or a combination thereof in order to bring the alkene concentration in the alkylate into the desired range will also have the effect of resetting the flow rates of the alkane or aromatic feed stream and of the alkene feed stream, and the reactor temperature to within their respective established control limits. When multiple sub-reaction zones are employed, the flow rates of the alkane or aromatic feed stream and of the alkene feed stream to each sub-reaction zone and each sub-reaction zone temperature are reset to within their respective established control limits.

The above outlined method will provide control for steady state operation and constant catalyst activity. An operator may decide what adjustments, if any, are needed in the process based upon the measured alkene concentration at different locations when the algorithm in the control system has reached a limit. A particular benefit of the invention is that specific operating parameters may be adjusted automatically in light of measured alkene concentrations at selected locations. In other words, operating parameter adjustments are paired with the alkene measurement locations most suitable for the particular operating parameter. More efficient control is achieved where the alkene feed stream and alkene feed stream flow rates and the reaction zone temperature are adjusted based solely on the alkene concentration determinations made on the reaction mixture in the reactor, and not incorporating determinations made on the alkylate product stream. Even greater control is achieved where alkene concentration determinations are made at each of multiple serially-connected sub-reaction zones. Each of the sub-reaction zones has independent reactant feed streams, thus the alkene feed stream flow rate, the alkane feed stream flow rate, and temperature of the sub reactor zone may be independently adjusted for each sub-reaction zone according to the corresponding alkene concentration measurements. Adjustments of flow rates and reaction zone temperatures may be sufficient for a period of time to maintain the amount of alkene within a desired range.

However, when space velocity and reaction zone temperatures can no longer be effectively adjusted, and high alkene concentrations are measured in the alkylate product stream, other operating parameters such as the flow rate of catalyst sent to the regenerator, the severity and duration of catalyst regeneration, treatment of the feed streams to remove contaminants that act as catalyst poisons, or a combination thereof may be adjusted. Note that the operating parameters here are adjusted solely based on the alkene concentration in the product alkylate stream.

It is contemplated that the type and frequency of operating parameter adjustments will vary from alkylation process to alkylation process, and over time within the same alkylation process. For example, repeated reaction zone alkene measurements will require a series of flow rate and temperature adjustments before the product alkylate alkene measurement indicates a single adjustment of the other parameters. Then the alkene measurement at the alkylate may indicate one or more adjustments to operating parameters such as the flow rate of catalyst sent to the regenerator, the severity and duration of catalyst regeneration, and treatment of the feed streams to remove contaminants that act as catalyst poisons. These may be followed by another series of flow rate and temperature adjustments as indicated by the reaction zone alkene measurements. However, the overall control of the alkylation process is enhanced through the multi-level approach of using one set of operating parameters for control based on the alkene concentration in the reaction zone(s) and simultaneously using another set of operating parameters for control based on the alkene concentration in the alkylate.

Furthermore, the invention may incorporate controlling the alkylation process without operator intervention. For example, the invention may automatically adjust an operating parameter according to a control algorithm so that the alkene concentration at a specific location is less than the predetermined maximum allowable concentration of alkene at that location. In this embodiment, once the concentration of alkene at a location has been determined, a suitable algorithm may be applied to determine the required changes in the operating parameters to effect a desired change in the alkene concentration. Suitable algorithms may be any of those commonly used for control including expert systems, multivariate regression, neural network modeling and partial least squares. The preferred algorithm is partial least squares.

It is further contemplated that the sequence of steps of control may vary upon application. For example, all the alkene concentration determinations may be performed at all the locations within the process, and then the corresponding operating parameters are adjusted. In other circumstances, however, the alkene concentration determination at a first location may immediately trigger a corresponding operating parameter adjustment before other alkene determinations at other locations are completed. Then the alkene determination at a second location may trigger another corresponding operating parameter adjustment, and so on. Furthermore, a combination of the two described approaches may also be successful in a given application.

Without intending any limitation on the scope of the present invention and as merely illustrative, this invention is explained below in specific terms as applied to one specific embodiment of the invention, the alkylation of 2-butene with isobutane to form mainly trimethylpentanes. The figure shows a single sub-reaction zone that is one in a series of interconnected sub-reaction zones that form the reaction zone of the alkylation process operated in a continuous mode. Catalyst, alkylation products, and unconverted reactant from a previous sub-reaction zone are introduced to sub-reaction zone 4 via line 2. The 2-butene feed stream in line 8 and the isobutane feed stream in line 6 are combined to form feed stream 10 and are adjusted to a predetermined temperature using heat exchanger 12 and introduced into sub-reaction zone 4. The feed is injected into the ah sub-reaction zone through a nozzle designed to obtain optimal mixing of the reaction feed and the hydrocarbon and catalyst already in the sub-reaction zone. The flow of coolant in line 14 to heat exchanger 12 is controlled via valve 30 to regulate the feed stream temperature. The temperature in sub-reaction zone 4 is monitored using thermocouple 16. A first Raman spectroscopy backscatter probe 18 is aligned with a quartz window in the housing of a slipstream carrying reaction mixture from sub-reaction zone 4 at a location near the input of feed stream 10. A second Raman spectroscopy backscatter probe 20 is aligned with a quartz window in the housing of the slipstream from sub-reaction zone 4 at a location downstream of the input of feed stream 10. Additionally, a third Raman spectroscopy backscatter probe is aligned with a quartz window in the housing of the overall alkylate product effluent (not shown). A solid state external cavity laser provides the excitation light which is conducted sequentially to each quartz window via the probes. The excitation light is impinged on the fluid and the Raman scattered light is collected and conducted to a monochomoter by the probes. The Raman scattered light is diffracted by a grating and the diffracted light passes through the exit slit of the monochomoter. The diffracted light impinges on a CCD detector and a signal is generated for the intensities of the different wavelengths of light. The specific scattered wavelengths of interest are those at Raman wave numbers of greater than 150 $cm^{-1}$ and less than 1850 $cm^{-1}$. The signals are sent to a controller 22 where the concentration of alkene in the reaction mixture and in the effluent are determined using partial least squares and where the conversion of alkene taking place in the reaction mixture between the location of probe 18 and the location of probe 20 is determined by difference. The total time for each analysis is about 30 seconds.

The measured concentration of alkene in the reaction mixture determined by probe 18 is then compared with a range of allowable concentrations of alkene in the reaction mixture for the location near the input of the feed stream. If the measured concentration of alkene in the reaction mixture is outside the range of allowable concentrations of alkene, controller 22 is used to automatically adjust, within established control limits, the flow rate of the isobutane feed stream in line 6 via electrical connection 24 and valve 26. If control limits have been reached, the controller 22 may indicate an alarm. The determined conversion of alkene in the reaction mixture between the location of probe 18 and probe 20 is then compared with a range of allowable conversions of alkene. If the measured conversion of alkene is outside the range of allowable conversions of alkene, controller 22 is used to automatically adjust, within established control limits, the flow rate of the alkene feed stream in line 8 or the flow rate of coolant in line 14 via electrical connection 24 and valves 28 and 30, respectively. If control limits have been reached, the controller 22 may indicate an alarm. The effluent of the sub-reaction zone is flowed via line 32 to a subsequent sub-reaction zone. The measured concentration of alkene in the overall product alkylate effluent is then compared with a range of allowable concentrations of alkene in the effluent. If the measured concentration of alkene in the effluent is outside the range of allowable concentrations of alkene, an expert system is used to automatically adjust an operating parameter including increasing the rate, frequency, severity, duration of catalyst regeneration, or a combination thereof. Adjustments to the rate, frequency, severity, duration of catalyst regeneration, or a combination thereof also result in resetting the flow rates of the feed streams and the temperature of the sub-reaction zone to within their respective control limits. The process is repeated to achieve ongoing control and enhanced performance. Each sub-reaction zone would be equipped with the system outlined above, and each sub-reaction zone is independently controlled for an increased level of overall control of the alkylation process.

It must be emphasized that the above description is merely illustrative of an embodiment and is not intended as an undue limitation on the generally broad scope of the invention. Moreover, while the description is narrow in scope, one skilled in the art will understand how to extrapolate to the broader scope of the invention. For example, operation of the invention where the probes are immersed in the fluid, where different lasers and detectors are used, and where any adjustments to the operating parameters are performed manually can be readily extrapolated from the foregoing description. Likewise, whereas the description above describes making all alkene measurements and then sequentially comparing the measured alkene or alkene conversion to the allowable range for each location, one could take a stepwise approach and make a first measurement and compare the result to the predetermined allowable range for that location and possibly even make operating parameter adjustments before taking a second alkene measurement at a second location and continuing the control in that fashion. Similarly, one skilled in the art would understand how depolarization ratios could be used in the invention to enhance the quantitation of alkenes.

What is claimed is:

1. A method for controlling a solid catalyst alkylation process having an alkene stream and a reactant stream introduced to an input location of a reaction zone, a reaction mixture in the reaction zone, and a product alkylate, said method comprising:
   a) measuring the Raman spectrum on-line over wave numbers from about 150 $cm^{-1}$ to about 1850 $cm^{-1}$, of:
      i) the reaction mixture in the reaction zone at a location near the input location,
      ii) the reaction mixture in the reaction zone at a location downstream of the input location and upstream of the product alkylate, and
      iii) the alkylate;
   b) determining the concentration of alkene in:
      i) the reaction mixture in the reaction zone at the location near the input location, A,
      ii) the reaction mixture in the reaction zone at the location downstream of the input location and upstream of the product alkylate, B,
      iii) and the alkylate, C,
   c) using the Raman spectra and a first, second, and third algorithm;
   d) comparing A with a predetermined range of desired concentrations of alkene in the reaction mixture in the reaction zone at the location near the input location, D; and adjusting, within established reactant stream flow rate control limits, when A is not within D, the flow rate of the reactant stream according to a fourth algorithm to cause A to fall within D;
   e) determining, from the difference between A and B, the conversion of alkene occurring between the location near the input location and the location downstream of the input location and upstream of the product alkylate, E, and comparing E with a predetermined range of desired alkene conversion values, F, and adjusting, within established alkene stream flow rate control limits and reactor temperature control limits, when E is not within F, an operating parameter selected from the group consisting of flow rate of the alkene stream, reactor temperature, and a combination thereof, according to a fifth algorithm to cause E to fall within F; and
   f) comparing C with a predetermined range of desired concentrations of alkene in the alkylate, G, and adjusting, when C is not within G, an operating parameter selected from the group consisting of severity of catalyst regeneration conditions, treatment of the alkene stream, treatment of the reactant stream, frequency of catalyst regeneration, rate of catalyst regeneration, and a combination thereof, according to a sixth algorithm to cause C to fall within G and to reset operating parameters selected from the group consisting of the flow rate of the reactant stream, the flow rate of the alkene stream, the reactor temperature, and a combination thereof, to within their respective established control limits.

2. The method of claim 1 further characterized by continuously repeating steps (a) through (e) to maintain A within D, E within F, and C within G.

3. The method of claim 1 wherein the reactant stream contains hydrocarbons selected from the group consisting of alkane hydrocarbons and aromatic hydrocarbons.

4. The method of claim 1 wherein the reactant stream contains alkane hydrocarbons having from about 4 to about 6 carbon atoms.

5. The method of claim 1 wherein the reactant stream contains benzene.

6. The method of claim 1 wherein the first, second, and third algorithms are selected from the group consisting of partial least squares, principal component regression, multiple linear regression, ratioed peak areas, multivariate statistical methods, principal component analysis, and neural networks.

7. The method of claim 1 wherein the fourth, fifth, and sixth algorithms are selected from the group consisting of neural networks, expert systems, multivariate regression, and partial least squares.

8. A method for controlling a solid catalyst alkylation process having an alkene stream and a reactant stream introduced to a input location of each of multiple sub-reaction-zones, $z_i$, where i in an integer from 2 to n, of a reaction zone, a reaction mixture in each sub-reaction-zone $z_i$, and a product alkylate, said method comprising:
   a) measuring the Raman spectrum on-line over wave numbers from about 150 $cm^{-1}$ to about 1850 $cm^{-1}$ of:
      i) the reaction mixture in each sub-reaction-zone $z_i$, at a location near the input location of that sub-reaction-zone $z_i$,
      ii) the reaction mixture in each sub-reaction-zone $z_i$, at a location downstream of the input location of that sub-reaction-zone $z_i$ and upstream of the alkylate, and
      iii) the alkylate;
   b) determining the concentration of alkene in:
      i) the reaction mixture in each sub-reaction-zone $z_i$ at the location near the input location of each sub-reaction-zone $z_i$, $A_{z_i}$,
      ii) the reaction mixture in each sub-reaction-zone $z_i$ at the location downstream of the input location of each sub-reaction-zone $z_i$, $B_{z_i}$ and upstream of the alkylate, and
      iii) the alkylate, C, c) using the Raman spectra and a first, second, and third algorithm;

d) comparing $A_{z_i}$ with a predetermined range of desired concentrations of alkene in the reaction mixture of the subreaction-zone $z_i$ at the location near the input location of the sub-reaction-zone $z_i$, $D_{z_i}$ and adjusting, within established reactant stream flow rate control limits for sub-reaction-zone $z_i$, when $A_{z_i}$ is not within $D_{z_i}$, the flow rate of the reactant stream to sub-reaction-zone $z_i$ according to a fourth algorithm to cause $A_{z_i}$ to fall within $D_{z_i}$;

e) determining, from the difference between $A_{z_i}$ and $B_{z_i}$, the conversion of alkene occurring between the location near the input location and the location downstream of the input location and upstream of the alkylate of each sub-reaction-zone $z_i$, $E_{z_i}$, and comparing $E_{z_i}$ with a predetermined range of desired alkene conversion values for each sub-reaction-zone $z_i$, $F_{z_i}$, and adjusting, within established alkene flow rate control limits for sub-reaction-zone $z_i$ and temperature control limits for sub-reaction-zone $z_i$, when $E_{z_i}$ is not within $F_{z_i}$, an operating parameter selected from the group consisting of flow rate of the alkene stream to sub-reaction-zone $z_i$, temperature of sub-reaction-zone $z_i$, and a combination thereof, according to a fifth algorithm to cause $E_{z_i}$ to fall within $F_{z_i}$; and f) comparing C with a predetermined range of desired concentrations of alkene in the alkylate, G, and adjusting, when C is not within G, an operating parameter selected from the group consisting of severity of catalyst regeneration conditions, treatment of the alkene stream, treatment of the reactant stream, frequency of catalyst regeneration, rate of catalyst regeneration, and a combination thereof, according to a sixth algorithm to cause C to fall within G and to reset operating parameters selected from the group consisting of the flow rate of the reactant streams to the sub-reaction zones, the flow rate of the alkene streams to the sub-reaction-zones, the temperatures of the sub-reaction zones, and a combination thereof, to within their respective established control limits.

9. The method of claim 8 further characterized by continuously repeating steps (a) through (e) to maintain $A_{z_i}$ within $D_{z_i}$, $E_{z_i}$ within $F_{z_i}$, and C within G.

10. The method of claim 8 wherein the reactant stream contains hydrocarbons selected from the group consisting of alkane hydrocarbons and aromatic hydrocarbons.

11. The method of claim 8 wherein the reactant stream contains alkane hydrocarbons having from about 4 to about 6 carbon atoms.

12. The method of claim 8 wherein the reactant stream contains benzene.

13. The method of claim 8 wherein the first, second, and third algorithms are selected from the group consisting of partial least squares, principal component regression, multiple linear regression, ratioed peak areas, multivariate statistical methods, principal component analysis, and neural networks.

14. The method of claim 8 wherein the fourth, fifth, and sixth algorithms are selected from the group consisting of neural networks, expert systems, multivariate regression, and partial least squares.

* * * * *